United States Patent
Moynahan et al.

(10) Patent No.: US 11,142,797 B2
(45) Date of Patent: Oct. 12, 2021

(54) BIOMARKERS FOR RESPONSE TO PI3K INHIBITORS

(71) Applicant: Memorial Sloan-Kettering Cancer Center, New York, NY (US)

(72) Inventors: Mary Ellen Moynahan, New York, NY (US); Alice Gaskell, Woodside, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 15/346,197

(22) Filed: Nov. 8, 2016

(65) Prior Publication Data

US 2017/0051361 A1    Feb. 23, 2017

Related U.S. Application Data

(63) Continuation of application No. PCT/US2015/029995, filed on May 8, 2015.

(60) Provisional application No. 62/004,518, filed on May 29, 2014, provisional application No. 61/992,173, filed on May 12, 2014, provisional application No. 61/991,165, filed on May 9, 2014.

(51) Int. Cl.
| | |
|---|---|
| *C12Q 1/6886* | (2018.01) |
| *C12Q 1/68* | (2018.01) |
| *A61K 31/4196* | (2006.01) |
| *A61K 31/566* | (2006.01) |

(52) U.S. Cl.
CPC ........ *C12Q 1/6886* (2013.01); *A61K 31/4196* (2013.01); *A61K 31/566* (2013.01); *C12Q 1/68* (2013.01); *C12Q 2600/118* (2013.01); *C12Q 2600/156* (2013.01); *C12Q 2600/158* (2013.01)

(58) Field of Classification Search
CPC .... A61K 31/4196; A61K 31/566; C12Q 1/68; C12Q 1/6886; C12Q 2600/106; C12Q 2600/118; C12Q 2600/156; C12Q 2600/158
See application file for complete search history.

(56) References Cited

U.S. PATENT DOCUMENTS

| 2012/0288863 A1 | 11/2012 | Detmer et al. |
| 2014/0044706 A1 | 2/2014 | Belvin et al. |

FOREIGN PATENT DOCUMENTS

| CN | 102 816 839 A | 12/2012 | |
| WO | WO 2012/052745 A1 | 4/2012 | |
| WO | WO 2013/015833 A2 | 1/2013 | |
| WO | WO 2013/049581 A1 | 4/2013 | |
| WO | WO 2013/144249 A1 | 10/2013 | |
| WO | WO 2013/182668 | * 12/2013 | |
| WO | WO-2014047109 A1 | * 3/2014 | ............. A61K 45/06 |

OTHER PUBLICATIONS

Elkabets et al. Sci Transl Med (2013), vol. 5, pp. 1-28 (Year: 2013).*
ChemID Plus Alpelisib [online] Retrieved from the internet, [Retrieved on Feb. 13, 2018] <url:https://chem.nlm.nih.gov/chemidplus/rn/1217486-61-7> (Year: 2018).*
Dawson et al. The New England Journal of Medicine (2013), vol. 368, pp. 1999-1209 (Year: 2013).*
Neidle, Stephen, ed. (Elsevier/Academic Press, 2008) (Year: 2008).*
Gura etal. (Science 1997) (Year: 1997).*
Johnson etal., (British J. of Cancer 2001) (Year: 2001).*
Juric et al. (Abstract P6-10-07, Cancer Research, Dec. 2012) (Year: 2012).*
Juric, IMPAKT-2013, Breast Cancer Conference (Year: 2013).*
Aljanabi et al., "Universal and rapid salt-extraction of high quality genomic DNA for PCR-based techniques," Nucl. Acids Res. 25(22):4692-4693 (1997).
Bachman et al., "The PIK3CA Gene is Mutated with High Frequency in Human Breast Cancers," Cancer Biol. Ther. 3(8):772-775 (2004).
Campbell et al., "Mutation of the PIK3CA Gene in Ovarian and Breast Cancer," Cancer Res. 64:7678-7681 (2004).
Cizkova et al, "PIK3CA mutation impact on survival in breast cancer patients and in ERα, PR and ERBB2-based subgroups," Breast Cancer Res. 14:R28 (2012).
Forshew et al., "Noninvasive Identification and Monitoring of Cancer Mutations by Targeted Deep Sequencing of Plasma DNA," Sci. Transl. Med. 4(136):136ra68 (2012).
Gustincich et al., "A Fast Method for High-Quality Genomic DNA Extraction from Whole Human Blood," BioTechniques 11(3):298-302 (1991).

(Continued)

*Primary Examiner* — Umamaheswari Ramachandran
(74) *Attorney, Agent, or Firm* — Baker Botts L.L.P.

(57) ABSTRACT

The presently disclosed subject matter relates to the use of one or more biomarkers to evaluate whether a PI3Kα inhibitor would produce an anti-cancer effect in a subject during the course of treatment with a PI3Kα inhibitor. It is based, at least in part, on the discovery that certain nucleotides can be isolated from the serum of patients undergoing cancer treatment and can be used as a biomarker to indicate the effectiveness of PI3K treatment on cancer growth. Accordingly, in a non-limiting embodiment, a method for determining whether an anti-cancer effect is likely being produced in a cancer by a PI3Kα inhibitor, comprises determining the presence and/or level of one or more PIK3CA biomarkers in one or more samples serially obtained during PI3Kα inhibitor treatment, where if the presence and/or level of a PIK3CA biomarker is increased, it is less likely that the PI3Kα inhibitor is having an anti-cancer effect on the cancer.

12 Claims, 9 Drawing Sheets
Specification includes a Sequence Listing.

(56) References Cited

OTHER PUBLICATIONS

Hammond et al., "Extraction of DNA from Preserved Animal Specimens for Use in Randomly Amplified Polymorphic DNA Analysis," Analytical Biochemistry 240:298-300 (1996).
Hayakawa et al., "Synthesis and biological evaluation of sulfonylhydrazone-substituted imidazo[1,2-α]pyridines as novel PI3 kinase p110α inhibitors," Bioorg. Med. Chem. 15:5837-5844 (2007).
International Search Report dated Nov. 4, 2015 in International Application No. PCT/US15/29995.
Karakas et al., "Mutation of the PIK3CA oncogene in human cancers," British Journal of Cancer 94:455-459 (2006).
Lee et al., "PIK3CA gene is frequently mutated in breast carcinomas and hepatocellular carcinomas," Oncogene 24: 1477-1480 (2005).
Sambrook et al., "Molecular Cloning: A Laboratory Manual," 1989, 2nd Ed., Cold Spring Harbour Laboratory Press: New York, N.Y.
Samuels et al., "High Frequency of Mutations of the PIK3CA Gene in Human Cancers," Science 304:554 (2004).
Schmidt-Kittler et al., "PI3Kα Inhibitors That Inhibit Metastasis," Oncotarget 1(5):339-348 (2010).
Sunnucks et al., "Microsatellite and Chromosome Evolution of Parthenogenetic Sitobion Aphids in Australia," Genetics 144:747-756 (1996).
Troxell, et al., "PIK3CA/AKT1 Mutations in Breast Carcinoma: a Comprehensive Review of Experimental and Clinical Studies," J. Clin. Exp. Pathol, S1:1-11 (2012).
Wu et al., "Discovery of novel morpholino—quinoxalines as PI3Kα inhibitors by pharmacophore-based screening," Med. Chem. Commun. 3:659-662 (2012).
Engelman et al., "Effective use of PI3K and MEK inhibitors to treat mutant Kras G12D and PIK3CA H1047R murine lung cancers," Nature Medicine 14(12):1351-1356 (2008).
Moynahan, et al., "Monitoring PIK3CA mutant allele fraction (AF) in cell-free DNA (cfDNA) in metastatic breast cancer (MBC) patients treated with PI3Kα-inhibitor plus letrozole (L) or exemestane (E)," Journal of Clinical Oncology 32(15) Suppl.:517 (2014).
Schneck et al., "Analysing the mutational status of PIK3CA in circulating tumor cells from metastatic breast cancer patients," Molecular Oncology 7:976-986 (2013).
Supplementary European Search Report dated Nov. 14, 2017 in Application No. EP 15789311.
Furet et al., "Discovery of NVP-BYL719 a potent and selective phosphatidylinositol-3 kinase alpha inhibitor selected for clinical evaluation," Bioorganic & Medicinal Chemistry Letters, 23(13):3741-3748 (2013).
Maira et al., "P13K inhibitors for cancer treatment: where do we stand?" Biochemical Society Transactions, 37:265-272 (2009).

\* cited by examiner

Pre-treatment CT with extensive hepatic tumor burden

PR by RECIST at C3D1, C5D1 and C8D1

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gagcaagagg ctttggagta t                                                 21

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gctgtttaat tgtgtggaag atcc                                              24

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
aatgatgcac atcat                                                        15
```

```
<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
tgaatgatgc acgtcat                                                    17
```

BIOMARKERS FOR RESPONSE TO PI3K INHIBITORS

PRIORITY CLAIM

This application is a continuation of International Patent Application No. PCT/US2015/029995, filed May 8, 2015, which claims priority to U.S. Provisional Patent Application Ser. No. 61/991,165, filed May 9, 2014, U.S. Provisional Patent Application Ser. No. 61/992,173, filed May 12, 2014, and U.S. Provisional Patent Application Ser. No. 62/004,518, filed May 29, 2014, the contents of which are incorporated by reference herein in their entireties.

SEQUENCE LISTING

The instant application contains a Sequence Listing which has been submitted electronically in ASCII format and is hereby incorporated by reference in its entirety. Said ASCII copy, created on Dec. 5, 2016, is named 072734_0427_SL.txt and is 1,309 bytes in size.

1. INTRODUCTION

This present invention relates to biomarkers which may be used to evaluate whether a PI3K inhibitor would produce an anti-cancer effect in a subject during the course of treatment with the PI3K inhibitor. As such, these biomarkers may be used in methods of treating cancer patients.

2. BACKGROUND OF THE INVENTION

Phosphatidylinositol 3-kinases (PI3Ks) are lipid kinases that are important in controlling signaling pathways involved in cell proliferation, motility, death and invasion, as well as in insulin signaling. Upon activation, PI3K catalyzes the phosphorylation of the cell membrane-embedded phosphatidylinositol 4,5-bisphosphate ($PIP_2$) to phosphatidylinositol 3,4,5-triphosphate ($PIP_3$). In turn, $PIP_3$, a critical phospholipid second messenger, acts as a docking site for signaling proteins, such as PDK1, to effect downstream cellular pathways critical for cell growth and survival. Class I PI3Ks contains four isoforms, p110α, p110β, p110δ and p110γ, which carry out non-redundant signaling functions. Mutations in phosphatidylinositol-4,5-bisphosphate 3-kinase catalytic subunit alpha isoform (PIK3CA), the gene encoding p110α, are frequently found in multiple human tumor types, such as colorectal cancer, breast cancer, ovarian cancer, endometrial carcinoma and hepatocellular carcinoma, suggesting that p110α is a key isoform for promoting tumor growth. In particular, in many tumors, the PI3K signaling pathway is constitutively activated. This is thought to be a critical step in mediating the transforming potential and growth stimulating activity of various oncogenes (i.e., HER2, EGFR, IGF1R).

The current standard of care in monitoring cancer patients undergoing treatment is the use of medical imaging and invasive techniques, such as biopsies. However, in certain circumstances, such biopsies can be deemed unsafe, impractical or not feasible. Therefore, there remains a need in the art for minimally invasive techniques that can allow real-time monitoring of the effectiveness of a particular cancer treatment within a patient. The discovery of circulating DNA, also called cell-free DNA, in the blood of a subject provides the opportunity to analyze genetic material originating from normal and/or tumor cells without the risks associated with invasive sampling methods. Cell free DNA fragments containing tumor-specific sequence alterations can be found in the cell free fraction of blood.

Accordingly, there is a need in the art for methods and/or biomarkers useful for monitoring the effectiveness of anti-cancer treatments, such as PI3K inhibitors, in a subject.

3. SUMMARY

The present disclosure relates to the use of one or more biomarkers to evaluate whether an anti-cancer effect is likely to be produced in a subject during the course of treatment with a PI3K inhibitor. It is based, at least in part, on the discovery that certain nucleotides, e.g., genomic DNA in free circulation, isolated from the serum of subjects undergoing cancer treatment, could be used as biomarkers to indicate the effectiveness or ineffectiveness, of PI3Kα treatment on cancer growth.

Accordingly, in non-limiting embodiments, the present subject matter provides for methods and kits for determining the presence and/or level of one or more biomarkers, e.g., mutant alleles of PIK3CA in cell free DNA, and methods of using such determinations in selecting and/or modifying a therapeutic regimen for a cancer patient.

In certain embodiments, the method for determining whether an anti-cancer effect is likely to be produced in a cancer of a subject by a PI3Kα inhibitor comprises determining the presence and/or level of one or more PIK3CA biomarkers in one or more body fluid samples obtained from a subject during PI3Kα inhibitor treatment, where if the presence and/or level of a PIK3CA biomarker increases, it is less likely that a PI3Kα inhibitor is having an anti-cancer effect on the cancer. In certain non-limiting embodiments, the method for determining whether an anti-cancer effect is likely to be produced in a cancer of a subject by an inhibitor of PI3Kβ, PI3Kγ, or PI3Kδ comprises determining the presence and/or level of one or more PIK3CB, PIK3CC, or PIK3CD biomarkers, respectively, in one or more body fluid samples obtained during inhibitor treatment, where if the presence and/or level of a biomarker increases, it is less likely that an inhibitor is having an anti-cancer effect on the cancer. This information may be advantageously used to avoid ineffective treatment and to redirect a subject to a more effective therapeutic regimen.

In certain embodiments, the method for determining whether an anti-cancer effect is likely to be produced in a cancer of a subject by a PI3Kα inhibitor comprises determining the presence and/or level of one or more PIK3CA biomarkers in one or more body fluid samples obtained during PI3Kα inhibitor treatment, where if the presence and/or level of a PIK3CA biomarker decreases, it is likely that a PI3Kα inhibitor is having an anti-cancer effect on the cancer. In certain non-limiting embodiments, the method for determining whether an anti-cancer effect is likely to be produced in a cancer of a subject by an inhibitor of PI3Kβ, PI3Kγ, or PI3Kδ comprises determining the presence and/or level of one or more PIK3CB, PIK3CC, or PIK3CD biomarkers, respectively, in one or more body fluid samples obtained during inhibitor treatment, where if the presence and/or level of a biomarker decreases, it is more likely that an inhibitor is having an anti-cancer effect on the cancer.

The present disclosure further provides methods for producing an anti-cancer effect in a subject comprising determining the presence and/or level of a PIK3CA biomarker in one or more body fluid samples of the subject obtained during PI3Kα inhibitor treatment, where if the presence and/or level of a PIK3CA biomarker is reduced, then continuing treatment of the subject with a therapeutically effective amount of a PI3Kα inhibitor, but if the presence and/or level of a PIK3CA biomarker increases, then discontinuing treatment with the PI3Kα inhibitor and optionally pursuing treatment of the subject with a therapeutically effective amount of another anti-cancer agent. Analogous methods can be performed using inhibitors that act on other PI3K isoforms and corresponding biomarkers.

In certain embodiments, the cancer can be liver cancer, brain cancer, cervical cancer, colorectal cancer, breast cancer, endometrial carcinoma, gastric cancer, cancers of the head and neck, bladder cancer, lung cancer, ovarian cancer, biliary tree cancer and hepatocellular carcinoma.

In certain embodiments, the one or more samples are plasma samples. The one or more samples can be obtained serially after initiation of PI3K inhibitor treatment. In certain embodiments, the one or more samples are serially obtained from the patient about every four weeks after initiation of treatment. Alternatively or additionally, the one or more samples are obtained serially from the patient about every two weeks after initiation of treatment.

In certain embodiments, the one or more PIK3CA biomarkers are mutations in the C2 domain, kinase domain and/or helical domain of PIK3CA which increases PIK3CA activity. In certain non-limiting embodiments, the one or more biomarkers are selected from the group consisting of the PIK3CA H1047R biomarker, PIK3CA E545K biomarker, PIK3CA E542K biomarker, PIK3CA E545G biomarker, PIK3CA E545Q biomarker, PIK3CA E545A biomarker, PIK3CA E545D biomarker, PIK3CA E545V biomarker, PIK3CA H1047L biomarker, PIK3CA H1047Y biomarker, PIK3CA E542Q biomarker, PIK3CA E542G biomarker, PIK3CA P539R biomarker, PIK3CA N345K biomarker, PIK3CA C420R biomarker, PIK3CA G1049R biomarker, PIK3CA E726K biomarker, PIK3CA R88Q biomarker, PIK3CA Q546K biomarker, PIK3CA Q546P biomarker, PIK3CA Q546R biomarker, PIK3CA Q546L biomarker or combinations thereof.

The present disclosure further provides kits for determining whether an anti-cancer effect is likely being produced in a cancer by a PI3Kα inhibitor, comprising a means for detecting a PIK3CA biomarker. In certain embodiments, the means for detecting a PIK3CA biomarker includes one or more sets of primers or probes specific for the PIK3CA biomarker.

4. BRIEF DESCRIPTION OF FIGURES

5. DETAILED DESCRIPTION

Figure 1:
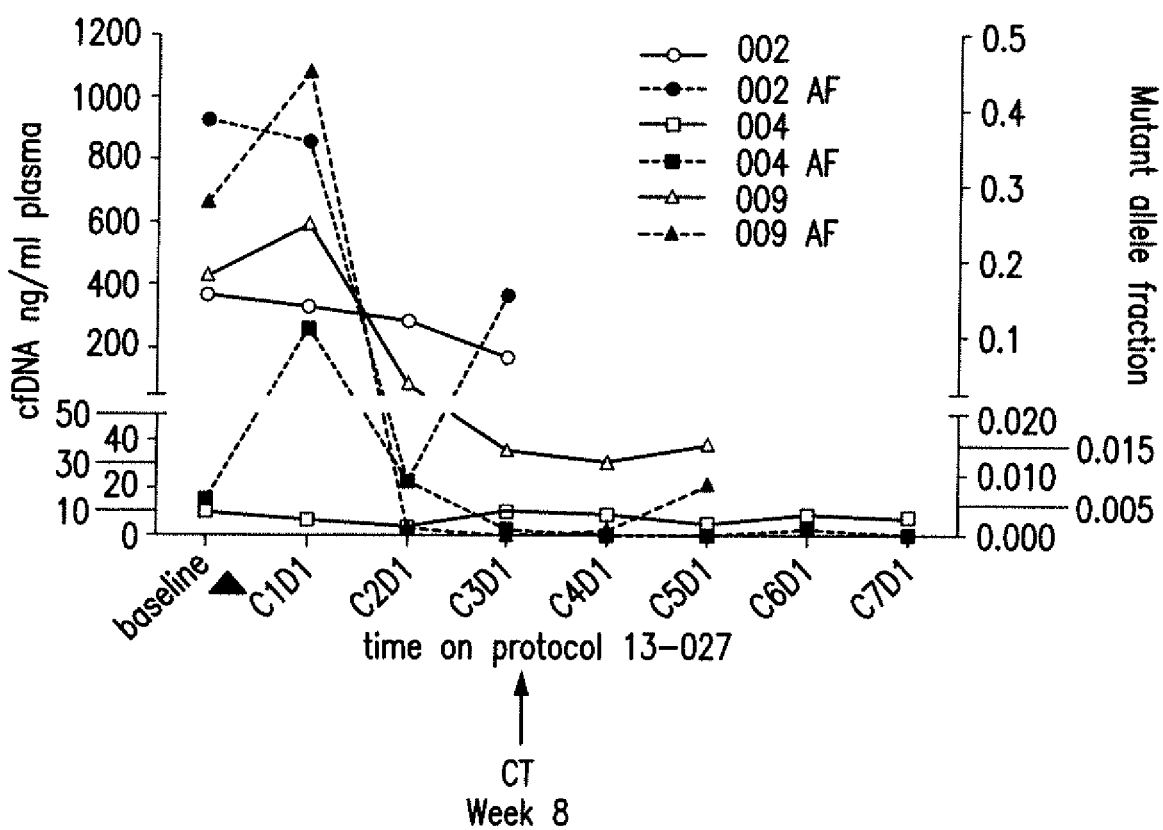
FIG. 1 shows the plasma concentrations of total cell free DNA (ng/ml) and tumor-specific mutant allele fractions in cell free DNA of PIK3CA E542K and E545K in patients being treated with a PI3Kα inhibitor.

For clarity and not by way of limitation the detailed description of the invention is divided into the following subsections:
(i) PIK3CA as a biomarker;
(ii) PI3Kα inhibitors;
(iii) cancer targets;
(iv) biomarker detection;
(v) methods of use; and
(vi) kits.

5.1 PIK3CA as a Biomarker

The present disclosure provides biomarkers for determining, during the course of treatment in a subject with a PI3Kα inhibitor, whether the PI3Kα inhibitor is likely effective at providing an anti-cancer effect on the cancer in the subject.

The term "biomarker" as used herein, includes nucleic acids of phosphatidylinositol-4,5-bisphosphate 3-kinase catalytic subunit alpha isoform, denoted herein as PIK3CA. In certain embodiments of the present disclosure, the biomarker is a nucleic acid that is related to the activity level of PIK3CA.

A "patient" or "subject," as used interchangeably herein, refers to a human or a non-human subject. Non-limiting examples of non-human subjects include non-human primates, dogs, cats, mice, rats, guinea pigs, rabbits, pigs, fowl, horses, cows, goats, sheep, cetaceans, etc.

In certain embodiments, the nucleic acids are present in a body fluid of the subject. For example, but not way of limitation, the biomarker of the present disclosure can be a nucleic acid, e.g., DNA, that is released into vascular system, present in circulation, e.g., blood or plasma, present in body fluid, e.g., plasma, serum, urine or pleural effusion or is extracellular, e.g., outside of (not located within) any cell, bound or unbound to the cell surface.

The biomarkers of the present disclosure can be obtained from a "biological sample" or "sample." A "biological sample" or "sample," as used interchangeably herein, refers to a sample of biological material obtained from a subject, including a biological fluid and/or body fluid, e.g., blood, plasma, serum, stool, urine, lymphatic fluid, ascites, ductal lavage, nipple aspirate, saliva, broncho-alveolar lavage, tears and cerebrospinal fluid. In certain non-limiting embodiments, the levels and/or presence of one or more biomarkers of the present disclosure are determined in one or more samples obtained from a subject, e.g., plasma samples.

In certain non-limiting embodiments, a biomarker is an allelic variant or mutation of the PIK3CA gene that results in the activation, constitutive activation and/or overactivation of PIK3CA, e.g., gain of function mutations. In certain limiting embodiments, a biomarker is an allelic variant or mutation of the PIK3CA gene or protein that results in the loss of functional PIK3CA protein.

In certain non-limiting embodiments, a PIK3CA biomarker is a nucleic acid having one or more insertions, deletions or substitutions relative to a reference PIK3CA gene described below. Such insertions, deletions or substitutions may result in a nonsense mutation, a frameshift mutation, a missense mutation or a termination relative to the reference PIK3CA gene and/or protein.

In a specific, non-limiting embodiment, a "reference," "reference control" or "control," as used interchangeably herein, may be a human PIK3CA nucleic acid having the sequence as set forth in NCBI database accession no. NG_012113.2, or a nucleic acid encoding a PIK3CA protein molecule that has the amino acid sequence set forth in NCBI database accession no. GI:126302584.

Reference PIK3CA nucleic acids for non-human species are known or can be determined according to methods known in the art, for example, where the sequence is the allele represented in the majority of the population of that species.

Where comparisons to a reference control level, quantity, expression and/or presence are referred to herein, the biomarker is assessed relative to the reference control level, quantity, expression and/or presence within the same species. For example, a human PIK3CA biomarker level and/or presence is compared with a human PIK3CA reference control level and/or presence.

In certain non-limiting embodiments, a PIK3CA biomarker for a human subject is the PIK3CA H1047R mutation.

In certain non-limiting embodiments, a PIK3CA biomarker for a human subject is the PIK3CA H1047Y mutation.

In certain non-limiting embodiments, a PIK3CA biomarker for a human subject is the PIK3CA H1047L mutation.

In certain non-limiting embodiments, a PIK3CA biomarker for a human subject is the PIK3CA E545K mutation.

In certain non-limiting embodiments, a PIK3CA biomarker for a human subject is the PIK3CA E545G mutation.

In certain non-limiting embodiments, a PIK3CA biomarker for a human subject is the PIK3CA E542K mutation.

In certain non-limiting embodiments, a PIK3CA biomarker comprises one or more mutations in the helical, kinase domain, adaptor-binding, Ras-binding, C2 domains or combinations thereof.

Additional non-limiting examples of PIK3CA biomarkers are disclosed in Samuels et al., Science (2004) 304(5670): 554; Campbell et al., Cancer Res. (2004) 64(21):7678-7681; Lee et al., Oncogene (2005) 24:1477-1480; Cizkova et al, Breast Cancer Res. (2012) 14(1):R28; Bachman et al., Cancer Biol. Ther. (2004) 3(8):772-775; and Karakas et al., British Journal of Cancer (2006) 94:455-459, the contents of which are herein incorporated by reference in their entities.

In certain non-limiting embodiments, a PIK3CA biomarker comprises one or more mutations in the helical domain of PIK3CA, which, for example, increases PIK3CA catalytic activity. In certain non-limiting embodiments, a PIK3CA biomarker comprises one or more mutations in the kinase domain of PIK3CA, which, for example, increases PIK3CA catalytic activity. In certain non-limiting embodiments, a PIK3CA biomarker comprises one or more mutations in the C2 domain of PIK3CA, which, for example, increases PIK3CA catalytic activity. In certain non-limiting embodiments, the mutated PIK3CA nucleotide sequence is at least 95 or at least 98 or at least 99 or at least 99.5 percent homologous to the reference control, described above. Sequence homology can be determined, for example, by software such as BLAST or FASTA.

In certain non-limiting embodiments, a PIK3CA biomarker comprises one or more mutations including the PIK3CA H1047R mutation, the PIK3CA E545K mutation, the PIK3CA E542K mutation, the PIK3CA E545G mutation, the PIK3CA E545Q mutation, the PIK3CA E545A mutation, the PIK3CA E545D mutation, the PIK3CA E545V mutation, the PIK3CA H1047L mutation, the PIK3CA H1047Y mutation, the PIK3CA E542Q mutation, the PIK3CA E542G mutation, the PIK3CA P539R mutation, the PIK3CA N345K mutation, the PIK3CA C420R mutation, the PIK3CA G1049R mutation, the PIK3CA E726K mutation, the PIK3CA R88Q mutation, the PIK3CA Q546K mutation, the PIK3CA Q546P mutation, the PIK3CA Q546R mutation, the PIK3CA Q546L mutation or combinations thereof.

5.2 PI3Kα Inhibitors

Non-limiting examples of PI3Kα inhibitors include compounds, molecules, chemicals, polypeptides and proteins that inhibit and/or reduce the expression and/or activity of PI3Kα. Additional non-limiting examples of PI3Kα inhibitors include ATP-competitive inhibitors of PI3Kα. In particular non-limiting embodiments, the PI3Kα inhibitor is derived from imidazopyridine or 2-aminothiazole compounds. Further non-limiting examples include BYL719, INK-1114, INK-1117, NVP-BYL719, SRX2523, LY294002, PIK-75, PKI-587, A66, CH5132799 and GDC-0032 (taselisib).

Further non-limiting examples of PI3Kα inhibitors are disclosed in Schmidt-Kittler et al., Oncotarget (2010) 1(5): 339-348; Wu et al., Med. Chem. Comm. (2012) 3:659-662; Hayakawa et al., Bioorg. Med. Chem. (2007) 15(17): 5837-5844; and PCT Patent Application Nos. WO2013/049581 and WO2012/052745, the contents of which are herein incorporated by reference in their entireties.

Further non-limiting examples of PI3Kα inhibitors include ribozymes, antisense oligonucleotides, shRNA molecules and siRNA molecules that specifically inhibit and/or reduce the expression or activity of PI3Kα. One non-limiting example of a PI3Kα inhibitor comprises an antisense, shRNA, or siRNA nucleic acid sequence homologous to at least a portion of a PI3Kα nucleic acid sequence, e.g., the nucleic acid sequence of a PI3Kα subunit such as PIK3CA, wherein the homology of the portion relative to the PI3Kα sequence is at least about 75 or at least about 80 or at least about 85 or at least about 90 or at least about 95 or at least about 98 percent, where percent homology can be determined by, for example, BLAST or FASTA software. In certain non-limiting embodiments, the complementary portion may constitute at least 10 nucleotides or at least 15 nucleotides or at least 20 nucleotides or at least 25 nucleotides or at least 30 nucleotides and the antisense nucleic acid, shRNA or siRNA molecules may be up to 15 or up to 20 or up to 25 or up to 30 or up to 35 or up to 40 or up to 45 or up to 50 or up to 75 or up to 100 nucleotides in length. Antisense, shRNA, or siRNA molecules may comprise DNA or atypical or non-naturally occurring residues, for example, but not limited to, phosphorothioate residues.

In certain non-limiting embodiments, the PI3Kα inhibitor can be used alone or in combination with one or more anti-cancer agents. An "anti-cancer agent," as used herein, can be any molecule, compound, chemical or composition that has an anti-cancer effect. Anti-cancer agents include, but are not limited to, chemotherapeutic agents, radiotherapeutic agents, cytokines, anti-angiogenic agents, apoptosis-inducing agents, anti-cancer antibodies, anti-cyclin-dependent kinase agents, and/or agents which promote the activity of the immune system including but not limited to cytokines such as but not limited to interleukin 2, interferon, anti-CTLA4 antibody, anti-PD-1 antibody, and/or anti-PD-L1 antibody. For example, but not by way of limitation, a PI3Kα inhibitor can be used in combination with letrozole or exemestane. "In combination with," as used herein, means that the PI3Kα inhibitor and the one or more anti-cancer agents are administered to a subject as part of a treatment regimen or plan. In certain embodiments, being used in combination does not require that the PI3Kα inhibitor and one or more anti-cancer agents are physically combined prior to administration or that they be administered over the same time frame.

5.3 Cancer Targets

Non-limiting examples of cancers that may be subject to the presently disclosed subject matter include liver cancer, brain cancer, cervical cancer, colorectal cancer, breast cancer, endometrial carcinoma, gastric cancer, cancers of the head and neck, bladder cancer, lung cancer, ovarian cancer, biliary tree cancer and hepatocellular carcinoma.

5.4 Biomarker Detection

A biomarker of the present disclosure can be isolated from a subject by any means known in the art or described herein. For example, but not by way of limitation, a biomarker, e.g., a cell free mutant allele of a PIK3CA nucleic acid, can be isolated from a biological sample obtained from a subject, such as a plasma sample, or other biological fluid, as described above.

There are several platforms that are known in the art and currently available to isolate cell free nucleic acids from biological samples. In certain embodiments, isolation of DNA from a biological samples is based on extraction methods using organic solvents such as a mixture of phenol and chloroform, followed by precipitation with ethanol (see, for example, J. Sambrook et al., "Molecular Cloning: A Laboratory Manual", 1989, 2nd Ed., Cold Spring Harbour Laboratory Press: New York, N.Y.). Additional non-limiting examples include salting out DNA extraction (see, for example, P. Sunnucks et al., Genetics, 1996, 144: 747-756; and S. M. Aljanabi and I. Martinez, Nucl. Acids Res. 1997, 25: 4692-4693), the trimethylannnonium bromide salts DNA extraction method (see, for example, S. Gustincich et al., BioTechniques, 1991, 11: 298-302) and the guanidinium thiocyanate DNA extraction method (see, for example, J. B. W. Hammond et al., Biochemistry, 1996, 240: 298-300).

There are also numerous different and versatile kits that can be used to extract DNA from bodily fluids and that are commercially available from, for example, BD Biosciences Clontech (Palo Alto, Calif.), Epicentre Technologies (Madison, Wis.), Gentra Systems, Inc. (Minneapolis, Minn.), MicroProbe Corp. (Bothell, Wash.), Organon Teknika (Durham, N.C.), and Qiagen Inc. (Valencia, Calif.). Sensitivity, processing time and cost may be different from one kit to another. One of ordinary skill in the art can easily select the kit(s) most appropriate for the particular sample to be analyzed.

The presently disclosed subject matter further provides methods for detecting and/or determining the presence and/or level of a nucleic acid PIK3CA biomarker. For example, but not by way of limitation, such methods include polymerase chain reaction (PCR), including real-time PCR, quantitative PCR, fluorescent PCR, RT-MSP (RT methylation specific polymerase chain reaction and digital PCR, in situ hybridization, fluorescent in situ hybridization ("FISH"), gel electrophoresis, radioimmunoassay, direct radio-labeling of DNA, sequencing and sequence analysis, microarray analysis and other techniques known in the art.

In certain embodiments, the presence and/or level of a PIK3CA biomarker, can be detected through the use of DROPLET DIGITAL™ PCR (ddPCR™), which is a method for performing digital PCR based on water-oil emulsion droplet technology. Alternatively or additionally, a biomarker disclosed herein can be detected through direct plasma sequencing by means of tagged-amplicon deep sequencing (see, for example, Forshew et al., Sci. Transl. Med. (2012) 4:136, p. 136).

In certain embodiments, the level and/or presence of one or more biomarkers in one or more samples of a patient are determined by sequencing, e.g., next generation sequencing. In certain embodiments, the level and/or presence of one or more biomarkers are determined using an microarray. In certain embodiments, the level and/or presence of one or more biomarkers are determined using an assay that comprises an amplification reaction, such as a polymerase chain reaction (PCR).

5.5 Methods of Use

The presently disclosure provides methods for monitoring patients undergoing anti-cancer treatment with a PI3Kα inhibitor. Early detection of an increase in the tumor burden and/or tumor size, for example, by the detection of an increase in one or more of the presently disclosed biomarkers in one or more biological samples of the subject, would allow modification of the current treatment, e.g., change in the anti-cancer agent being administered to the subject, to avoid ineffective treatment and improve the subject's possibility of survival.

Accordingly, the present disclosure provides methods for determining, during the course of treatment of a subject having cancer with a PI3Kα inhibitor, whether an anti-cancer effect is likely being produced by the PI3Kα inhibitor. In certain embodiments, the methods include determining the presence and/or level of a biomarker in one or more serially collected samples of a patient, wherein if the presence and/or level of the biomarker decreases in the later collected samples, there is an increased likelihood that the PI3Kα inhibitor is having an anti-cancer effect.

PIK3CA biomarkers are described in section 5.1 above. PI3Kα inhibitors are described in section 5.2 above. Cancers suitable for treatment are described above in section 5.3. Methods of detecting a presently disclosed biomarker are described above in section 5.4.

In certain embodiments, the one or more samples are collected serially during the course of treatment with a PI3Kα inhibitor. For example, but not by way of limitation, the level and/or presence of a biomarker in a patient can be analysed during a course of treatment with a PI3Kα inhibitor through serial sampling. In certain embodiments, one or more samples can be obtained from a patient undergoing treatment about every 5 weeks, about every 4 weeks, about every 3 weeks, about every 2 weeks, about every week, about every 6 days, about every 5 days, about every 4 days, about every 3 days or about every 2 days. In certain non-limiting embodiments, one or more samples can be obtained from a patient about every 2 weeks. In certain embodiments, one or more samples can be obtained from a patient about every 28 days. In certain embodiments, one or more samples can be obtained from a patient on day 1 and on the last day, e.g., day 28, of one or more treatment cycles.

In certain embodiments, the one or more biological samples can be obtained prior to treatment with a PI3Kα inhibitor, after initiation of treatment and during treatment with the same or different PI3Kα inhibitor. For example, and not by way of limitation, one or more samples obtained during the course of treatment can be compared to a sample obtained prior to treatment or during initiation of treatment to determine the presence and/or change in the mutant allele fraction of a biomarker.

In certain non-limiting embodiments, the present disclosure provides for a method of determining whether an anti-cancer effect is likely being produced in a cancer by a PI3Kα inhibitor, comprising obtaining one or more samples sequentially from a patient undergoing treatment with a PI3Kα inhibitor, and determining, in each sample, the presence and/or level of a PIK3CA biomarker, where if the presence and/or level of the biomarker decreases, it is likely that the PI3Kα inhibitor is producing an anti-cancer effect on the cancer.

In certain non-limiting embodiments, a decrease in the mutant allele fraction of a PIK3CA biomarker, which indicates that a PI3Kα inhibitor is more likely producing an anti-cancer effect on the cancer, can be greater than about 70%, greater than about 80%, greater than about 85%, greater than about 86%, greater than about 87%, greater than about 88%, greater than about 89%, greater than about 90%, greater than about 91%, greater than about 92%, greater than about 93%, greater than about 94%, greater than about 95%, greater than about 96%, greater than about 97%, greater than about 98% or greater than about 99%.

In certain non-limiting embodiments, a decrease in the mutant allele fraction of a PIK3CA biomarker of less than about 25%, less than about 20%, less than about 15%, less than about 10%, less than about 9%, less than about 8%, less than about 7%, less than about 6%, less than about 5%, less than about 4%, less than about 3%, less than about 2% or less than about 1% may indicate that it is less likely that a PI3Kα inhibitor is producing an anti-cancer effect on the cancer.

In certain embodiments, a decrease in the mutant allele fraction of a PIK3CA biomarker of greater than about 90% in one or more samples obtained after treatment, as compared to a sample obtained prior to treatment, may indicate that a PI3Kα inhibitor is more likely producing an anti-cancer effect.

In certain embodiments, a decrease in the mutant allele fraction of a PIK3CA biomarker of greater than about 90% for two or more samples obtained during PI3Kα inhibitor treatment may indicate that a PI3Kα inhibitor is more likely producing an anti-cancer effect. In certain embodiments, a sample can be obtained on day 1 of a treatment cycle and a sample can be obtained on the last day, e.g., day 28, of the treatment cycle.

In certain embodiments, a decrease in the mutant allele fraction of a PIK3CA biomarker of greater than about 90% for two or more samples obtained after initiation of treatment, as compared to a sample obtained prior to treatment, may indicate that a PI3Kα inhibitor is more likely producing a continued anti-cancer effect.

In certain embodiments, a decrease in the mutant allele fraction of a PIK3CA biomarker of less than about 25% in one or more samples obtained after initiation of treatment, as compared to a sample obtained prior to treatment, may indicate that a PI3Kα inhibitor is less likely producing an anti-cancer effect.

An "anti-cancer effect," as used herein, refers to one or more of a reduction in aggregate cancer cell mass, a reduction in cancer cell growth rate, a reduction in cancer cell proliferation, a reduction in tumor mass, a reduction in tumor volume, a reduction in tumor cell proliferation, a reduction in tumor growth rate, and/or a reduction in tumor metastasis.

In certain non-limiting embodiments, the present invention provides for a method of determining whether an anti-cancer effect is likely being produced in a cancer by a PI3Kα inhibitor, comprising obtaining one or more samples sequentially from a patient undergoing treatment with a PI3Kα inhibitor, and determining, in each sample, the presence and/or level of a PIK3CA biomarker, where if the presence and/or level of the biomarker increases, it is more likely that the PI3Kα inhibitor is not producing an anti-cancer effect on the cancer.

In certain embodiments, if the presence and/or level of a PIK3CA biomarker decreases over the course of treatment with a PI3Kα inhibitor, the method can further include resuming and/or continuing treatment of the subject with a therapeutically effective amount of a PI3Kα inhibitor. For example, and not by way of limitation, if the presence and/or level of a PIK3CA biomarker decreases greater than about 90%, the method can further include resuming and/or continuing treatment of the subject with a therapeutically effective amount of a PI3Kα inhibitor. In certain non-limiting embodiments, the PI3Kα can be the same or different from the PI3Kα inhibitor administered during the determination of the change in PIK3CA biomarker presence and/or levels in the subject. A therapeutically effective amount is an amount that is able to achieve one or more of an anticancer effect, prolongation of survival and/or prolongation of period until relapse.

In certain non-limiting embodiments, the PI3Kα inhibitor used to treat the subject after the detection of a decrease in the presence and/or levels of a biomarker may be of the same or different chemical class than the PI3Kα inhibitor administered during the determination of the biomarker change in the subject. In certain non-limiting embodiments, the PI3Kα inhibitor used to treat the subject after the detection of a decrease in the presence and/or levels of a biomarker may function by a similar or different mechanism than the PI3Kα inhibitor administered during the determination of the biomarker change in the subject.

In certain embodiments, if the presence and/or level of a PIK3CA biomarker increases over the course of treatment with a PI3Kα inhibitor, the method can further include initiating treatment with another modality, for example, one or more alternative chemotherapeutic agents; radiotherapeutic agent; anti-angiogenic agent; apoptosis-inducing agent; anti-cancer antibody; agents which promote the activity of the immune system including but not limited to a cytokine such as but not limited to interleukin 2 or interferon, anti-CTLA4 antibody, anti-PD-1 antibody, and/or anti-PD-L1 antibody, letrozole or exemestane.

As used herein, "determining the presence and/or level" of biomarker refers to quantitative measurements as well as detecting the presence or absence of the biomarker. In certain embodiments, the level of a biomarker in sample can refer to the level of the biomarker compared to the reference control, as a percentage or a fraction (referred to herein as the mutant allele fraction). For example, and not by way of limitation, a mutant allele fraction can be the ratio of the level of a biomarker, e.g., mutant allele of PIK3CA, to the level of a reference control in the same sample. As described above in section 5.1, in certain embodiments, the reference control can be the allele of PIK3CA present in the majority of the population.

Alternatively or additionally, the level of a biomarker in a sample can refer to the total amount of the biomarker in the sample. For example, and not by way of limitation, the level of a biomarker can be the number of molecules of the biomarker (e.g., number of copies of the nucleic acid biomarker molecules) or the concentration of the biomarker in terms of weight per volume of biological sample, e.g., plasma.

5.6 Kits

In certain non-limiting embodiments, the present invention provides for kits for determining the effectiveness of treatment with a PI3Kα inhibitor in a subject having cancer, comprising a means for detecting one or more biomarkers set forth in section 5.1.

Types of kits include, but are not limited to, packaged biomarker-specific probe and primer sets (e.g., TaqMan probe/primer sets), arrays/microarrays, which further contain one or more probes, primers, biomarker-specific beads or other reagents for detecting one or more biomarkers of the present invention.

In a specific, non-limiting embodiment, a kit may comprise a pair of oligonucleotide primers, suitable for polymerase chain reaction (PCR) or nucleic acid sequencing, for detecting the biomarker(s) to be identified. A pair of primers may comprise nucleotide sequences complementary to a biomarker set forth above, and be of sufficient length to selectively hybridize with said biomarker. Alternatively, the complementary nucleotides may selectively hybridize to a specific region in close enough proximity 5' and/or 3' to the biomarker position to perform PCR and/or sequencing. Multiple biomarker-specific primers may be included in the kit to simultaneously assay large number of biomarkers.

The kit may also comprise one or more polymerases, reverse transcriptase, and nucleotide bases, wherein the nucleotide bases can be further detectably labeled. For example, in certain embodiments, the kits may comprise containers (including microliter plates suitable for use in an automated implementation of the method), each with one or more of the various reagents (typically in concentrated form) utilized in the methods, including, for example, pre-fabricated microarrays, buffers, the appropriate nucleotide triphosphates (e.g., dATP, dCTP, dGTP and dTTP, or rATP, rCTP, rGTP and UTP), reverse transcriptase, DNA polymerase, RNA polymerase, and one or more probes and primers of the present invention (e.g., appropriate length poly(T) or random primers linked to a promoter reactive with the RNA polymerase).

In certain non-limiting embodiments, a primer may be at least about 10 nucleotides or at least about 15 nucleotides or at least about 20 nucleotides in length and/or up to about 200 nucleotides or up to about 150 nucleotides or up to about 100 nucleotides or up to about 75 nucleotides or up to about 50 nucleotides in length.

In a further non-limiting embodiment, the oligonucleotide primers may be immobilized on a solid surface or support, for example, on a microarray, wherein the position of each oligonucleotide primer bound to the solid surface or support is known and identifiable. The terms "arrays," "microarrays," and "DNA chips" are used herein interchangeably to refer to an array of distinct polynucleotides affixed to a substrate, such as glass, plastic, paper, nylon or other type of membrane, filter, chip, bead, or any other suitable solid support. The polynucleotides can be synthesized directly on the substrate, or synthesized separate from the substrate and then affixed to the substrate. The arrays are prepared using known methods.

In a specific, non-limiting embodiment, a kit may comprise at least one nucleic acid probe, suitable for in situ hybridization or fluorescent in situ hybridization, for detecting the biomarker(s) to be identified. Such kits will generally comprise one or more oligonucleotide probes that have specificity for various biomarkers. Means for testing multiple biomarkers may optionally be comprised in a single kit.

In one specific non-limiting embodiment, a kit may comprise one or more pairs of primers, probes or microarrays suitable for detecting one or more PIK3CA biomarkers including the PIK3CA H1047R biomarker, PIK3CA E545K biomarker, PIK3CA E542K biomarker, the PIK3CA E545G biomarker, PIK3CA E545Q biomarker, PIK3CA E545A biomarker, PIK3CA E545D biomarker, PIK3CA E545V biomarker, PIK3CA H10471, biomarker, PIK3CA H1047Y biomarker, PIK3CA E542Q biomarker, PIK3CA E542G biomarker, PIK3CA P539R biomarker, PIK3CA N345K biomarker, PIK3CA C420R biomarker, PIK3CA G1049R biomarker, PIK3CA E7261<biomarker, PIK3CA R88Q biomarker, PIK3CA Q546K biomarker, PIK3CA Q546P biomarker, PIK3CA Q546R biomarker, PIK3CA Q546L biomarker or combinations thereof.

In one specific non-limiting embodiment, a kit may comprise a pair of primers, a probe or microarray suitable for detecting the PIK3CA E545K mutation biomarker.

In one specific non-limiting embodiment, a kit may comprise a pair of primers, a probe or microarray suitable for detecting the PIK3CA E545G mutation biomarker.

In one specific non-limiting embodiment, a kit may comprise a pair of primers, a probe or microarray suitable for detecting the PIK3CA E542K mutation biomarker.

In one specific non-limiting embodiment, a kit may comprise a pair of primers, a probe or microarray suitable for detecting the PIK3CA H1047Y mutation biomarker.

In one specific non-limiting embodiment, a kit may comprise a pair of primers, a probe or microarray suitable for detecting the PIK3CA H1047R mutation biomarker.

In one specific non-limiting embodiment, a kit may comprise a pair of primers, a probe or microarray suitable for detecting the PIK3CA H1047L mutation biomarker.

In certain non-limiting embodiments, where the measurement means in the kit employs an array, the one or more biomarkers set forth above may constitute at least 10 percent or at least 20 percent or at least 30 percent or at least 40 percent or at least 50 percent or at least 60 percent or at least 70 percent or at least 80 percent of the species of markers represented on the microarray.

In certain non-limiting embodiments, a biomarker detection kit may comprise one or more one or more probes, primers, microarrays/arrays, beads, detection reagents and other components (e.g., a buffer, enzymes such as DNA polymerases or ligases, chain extension nucleotides such as deoxynucleotide triphosphates, and in the case of Sanger-type DNA sequencing reactions, chain terminating nucleotides, and the like) to detect the presence and/or level of a reference control. Non-limiting examples of a reference control are described above in section 5.1.

In certain non-limiting embodiments, a kit can further include instructions for using the kit to detect the biomarker of interest. For example, the instructions can describe that a decrease in the level and/or presence of a biomarker, set forth herein, in serial samples from a patient undergoing treatment with a PI3K inhibitor, is indicative of a likelihood of an anti-cancer effect in a cancer by a PI3K inhibitor.

Alternatively or additionally, the instructions can further describe that an increase in the level and/or presence of a biomarker, set forth herein, in serial samples from a patient undergoing treatment with a PI3K inhibitor, is indicative of an increased possibility of an anti-cancer effect in a cancer by the PI3K inhibitor.

The following examples are offered to more fully illustrate the disclosure, but are not to be construed as limiting the scope thereof.

6. EXAMPLE 1

Monitoring PIK3CA Mutant Allele Fraction of Cell Free DNA in Metastatic Breast Cancer Patients Treated with a PI3Kα-Inhibitor, in Combination with Letrozole or Exemestane In this example, results of a correlative aim assessing serial mutant allele fraction in a phase I study of a PI3Kα-inhibitor, BYL719, with letrozole (L) or exemestane (E) in metastatic breast cancer patients are reported. Tumor-derived cell free DNA (cfDNA) was extracted from the plasma patient with tumors that harbored activating mutations and serially quantified by droplet digital PCR (ddPCR). These results indicate that mutant allele fractions may be predictive of target-directed therapy for initial response and evolving resistance.

6.1. Materials and Methods

PIK3CA status of tumors within patients was determined by molecular analysis of the tumor. It was determined that 8 patients were mutant for PIK3CA, 5 patients were wild-type for PIK3CA and 1 patient was unknown. Plasma samples were collected at baseline and on day 1 of each 28 day cycle while on the protocol. Cell free DNA was extracted using QIAamp Circulating nucleic acid kit (Qiagen) and quantified by KAPA human genomic DNA qPCR (Kapa Biosystems). Allele specific assays for PIK3CA E542K, E545K, H1047R and H1047L mutations were designed for quantification on BioRad QX200 DROPLET DIGITAL™ PCR System. For example, to detect and quantify the PIK3CA H1047R mutation, a forward primer (GAGCAAGAGGCTTTGGAGTAT) and reverse primer (GCTGTTTAATTGTGTGGAAGATCC) were used for thermocycling in conjunction with a TAQMAN® probe (VIC-AATGATGCACaTCAT-MGBNFQ) for the wild type PIK3CA 3140A PIK3CA sequence and a TAQMAN® probe (6FAM-TGAATGATGCACgTCAT-MGBNFQ) for the PIK3CA 3140G mutation. Mutant allele fraction was determined from the counts for mutant as compared to wild-type in the sample. The detection limit for each assay was calculated from the number of events detected.

Figure 2:
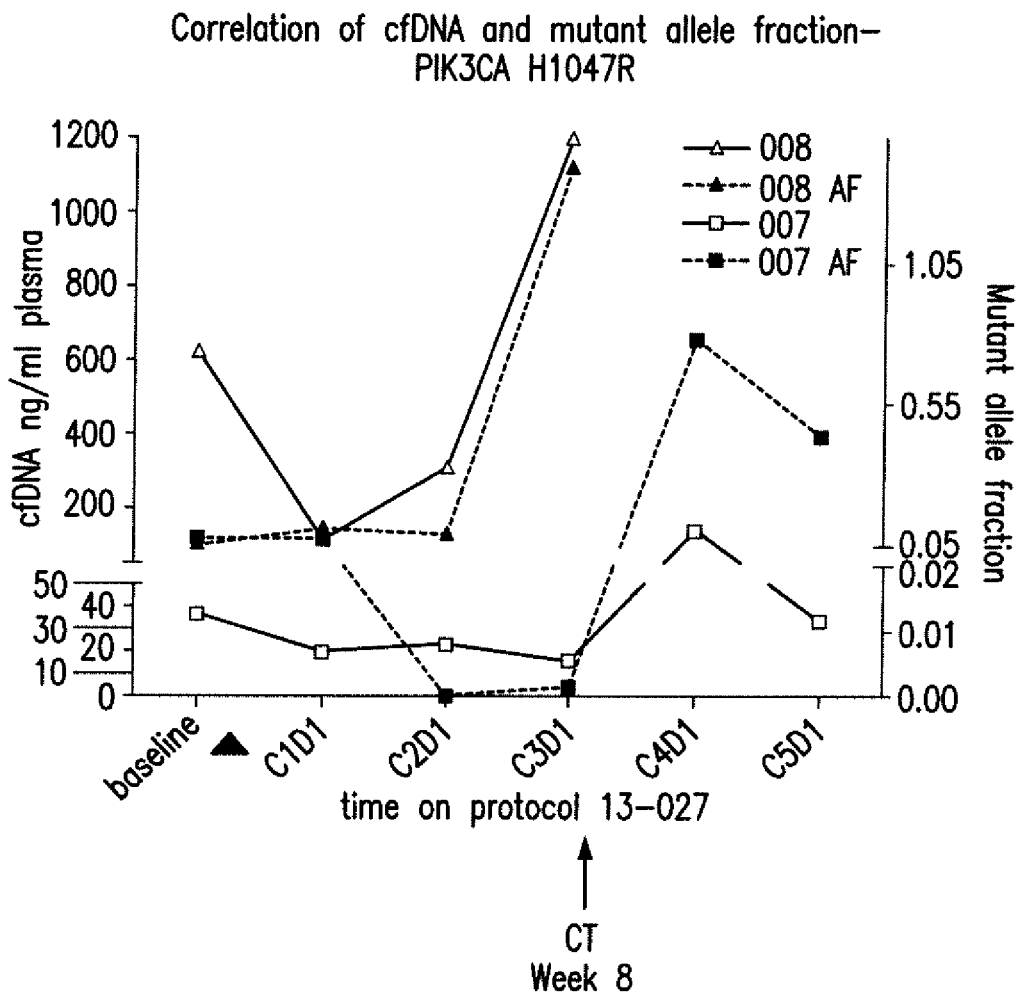
FIG. 2 shows the plasma concentrations of total cell free DNA (ng/ml) and tumor-specific mutant allele fractions in cell free DNA of PIK3CA H1047R in patients being treated with a PI3Kα inhibitor.

6.2. Results 5 out of 8 patients with PIK3CA mutation were evaluated by ddPCR having received treatment for at least 2 cycles with the PI3Kα-inhibitor. In the plasma of 4 patients, we identified a brisk decrease in PIK3CA mutant allele fraction at cycle 2, day 1 (C2D1) ranging from 91.8-99.6% decrease from baseline (see, for example, FIG. 1; 002 AF, 004 AF and 009 AF). All 4 patients had stable or responding disease as best response. In 1 patient, later determined to have disease progression, there was a small change (19% decrease) in PIK3CA mutant allele fraction at C2D1 with a 16× increase in mutant allele fraction at cycle 3 (FIG. 2, 008 AF). Ongoing responses result in a persistent low (>98% decrease) or undetectable mutant alleles (see, for example, FIG. 1; 004AF and 009 AF). In 1 patient, with a transient response, the marked decrease in mutant allele fraction at C2D1 was followed by an increase at cycle 3 predicting the patient's clinical progression (FIG. 1, 002 AF).

6.3. Discussion

Targeted therapies directed towards specific oncogene mutations may be assessed serially by ddPCR to confirm mutant target sensitivity. Assessment for early tumor resistance may allow a more rapid treatment change with real-time monitoring of target mutant alleles. Additionally, the detection of tumor derived fragments of DNA in a blood sample provides the opportunity for relatively non-invasive serial assessment of the genetic alterations harbored in the tumor, which can be helpful in the exploration of the more effective and better tolerated dosing schedules. Further, the analysis of cfDNA can be used to determine tumor mutation status for patients in whom a biopsy is not feasible and serial assessment for new genetic alterations that occur during tumor progression and therapeutic resistance.

7. EXAMPLE 2

Additional Monitoring of the PIK3CA Mutant Allele Fraction of Cell Free DNA in Metastatic Breast Cancer Patients Treated with a PI3Kα-Inhibitor, in Combination with Letrozole or Exemestane

7.1. Materials and Methods

Peripheral blood samples were processed by separating the plasma from the cellular fraction in a clinical hematology lab by centrifugation at 2000×g for 10 minutes. Plasma underwent a second centrifugation at 16,000×g for 10 minutes and stored frozen at −80 degrees until further processing.

Cell free DNA (cfDNA) was extracted from 2-5 ml of plasma using the QIAamp Circulating Nucleic Acid Kit (Qiagen). The concentration and integrity of cfDNA was determined by qPCR using the KAPA Human Genomic DNA quantification and QC kit (KAPAbiosystems). This method generated standard curves based on the amplification of a 41 bp, 129 bp and 305 bp fragment of a conserved single copy human gene. The ratio of the amplified 129 bp quantity to the 41 bp quantity was used as a measure of DNA quality.

Figure 3:
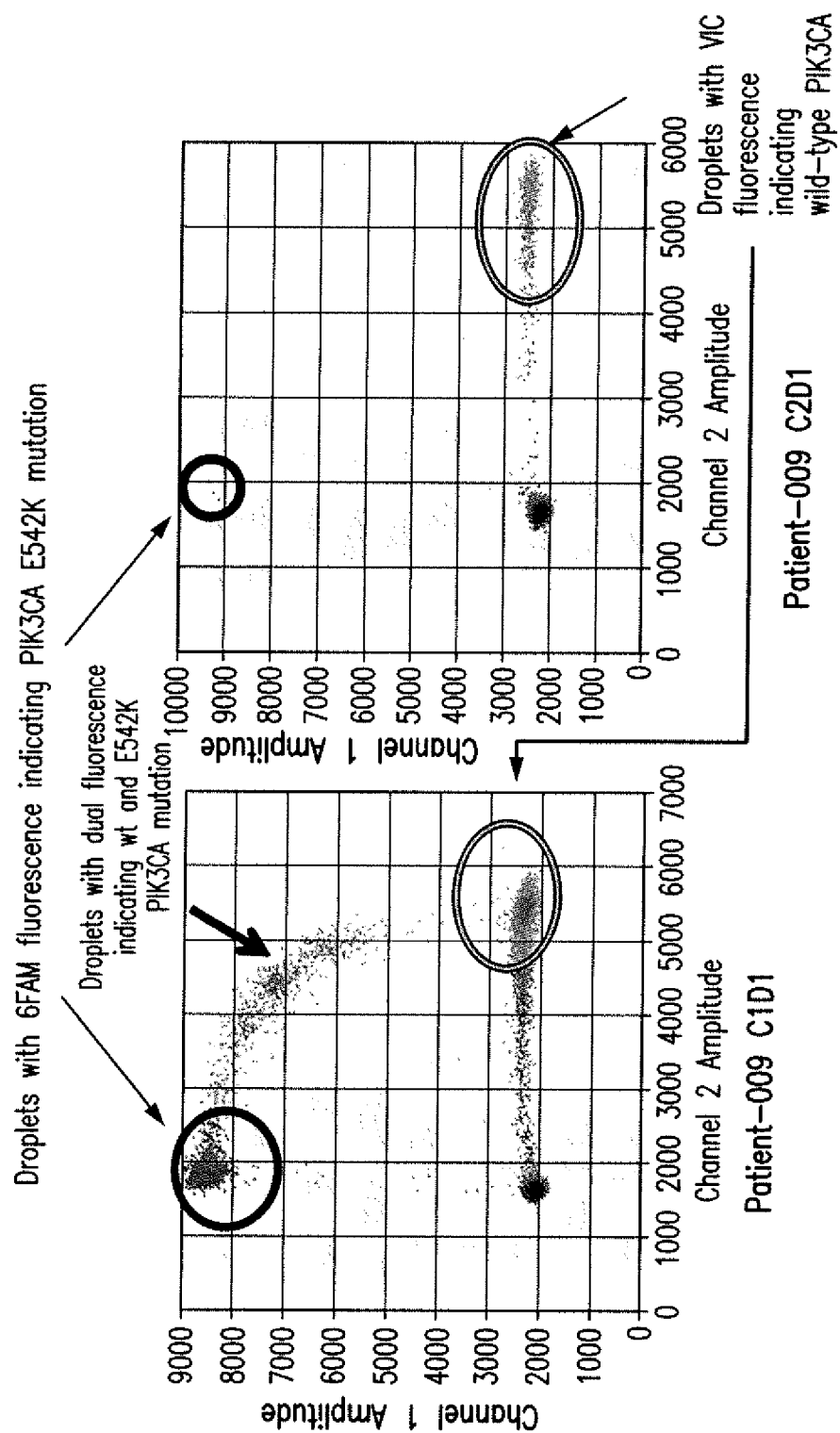
FIG. 3 shows a representation of a serial PIK3CA E542K mutation analysis by ddPCR from cell free DNA.

Allele specific assays for PIK3CA E542K, E545K, H1047R and H1047L mutations were designed for quantification on BioRad QX200 Droplet Digital PCR System. The Droplet digital PCR method included the generation of droplets with cfDNA templates, reactions primers and TAQMAN probes, followed by PCR. Droplets are then counted and scored for fluorescent wild-type or mutant probes. Mutant allele fraction was determined from the counts for mutant as compared to wild-type alleles. A representative example of serial PIK3CA E542K mutation analysis by ddPCR from cfCDNA is shown in FIG. 3. The lower limit of detection for each assay is calculated from the number of events detected.

7.2. Results

In all patients with tumors that were mutated for PIK3CA, a cfPIK3CA mutant allele was detected in the patient's plasma sample (TABLE 1). For example, in patients 002 and 013, the PIK3CA mutant allele E545K was detected by ddPCR. In patients 007 and 008 that had tumors with mutations in PIK3CA, the PIK3CA H1047R mutant allele was detected by ddPCR of circulating DNA, indicating that PIK3CA mutant allele fractions in cell free DNA can be used to monitor therapeutic treatments.

Figure 4:
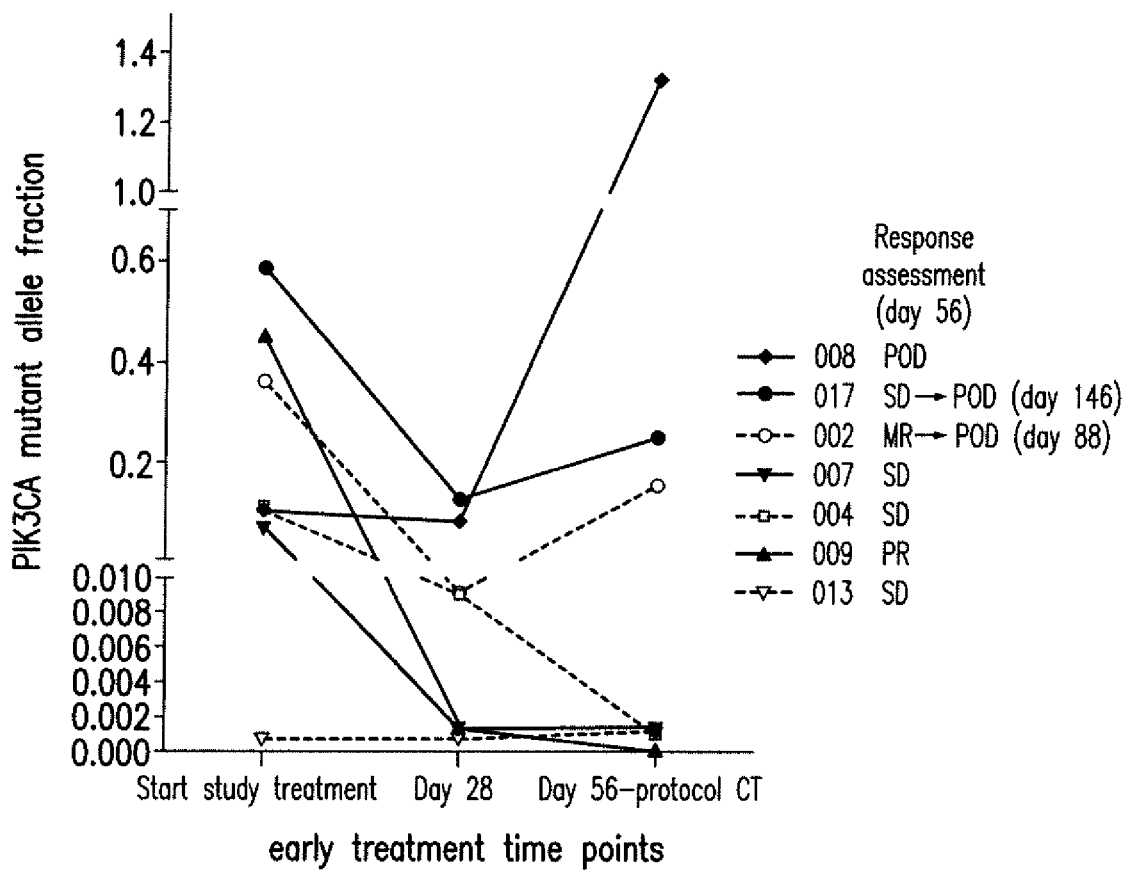
FIG. 4 shows the measurements of the cell free PIK3CA mutant allele fraction at day 28 for 7 patients being treated with a PI3Kα inhibitor.

As shown in TABLE 2, cfPIK3CA mutant allele fractions demonstrated a brisk decrease at day 28 in 5 out of 6 patients with stable and responding disease (FIG. 4). In patients 007 and 004 which demonstrated stable disease while on the study, exhibited greater than 90% decrease in mutant allele fraction by day 28. In patient 002, the cfPIK3CA E545K mutant allele fraction in response to treatment with BYL719 and letrozole decreased by 97.4% at day 28 (C2D1), which was followed by a 17 fold increase at C3D1 (FIGS. 1 and 4). Clinically, the patient had a 29% decrease in tumor volume by RECIST but then had rapid disease progression.

Figure 5:
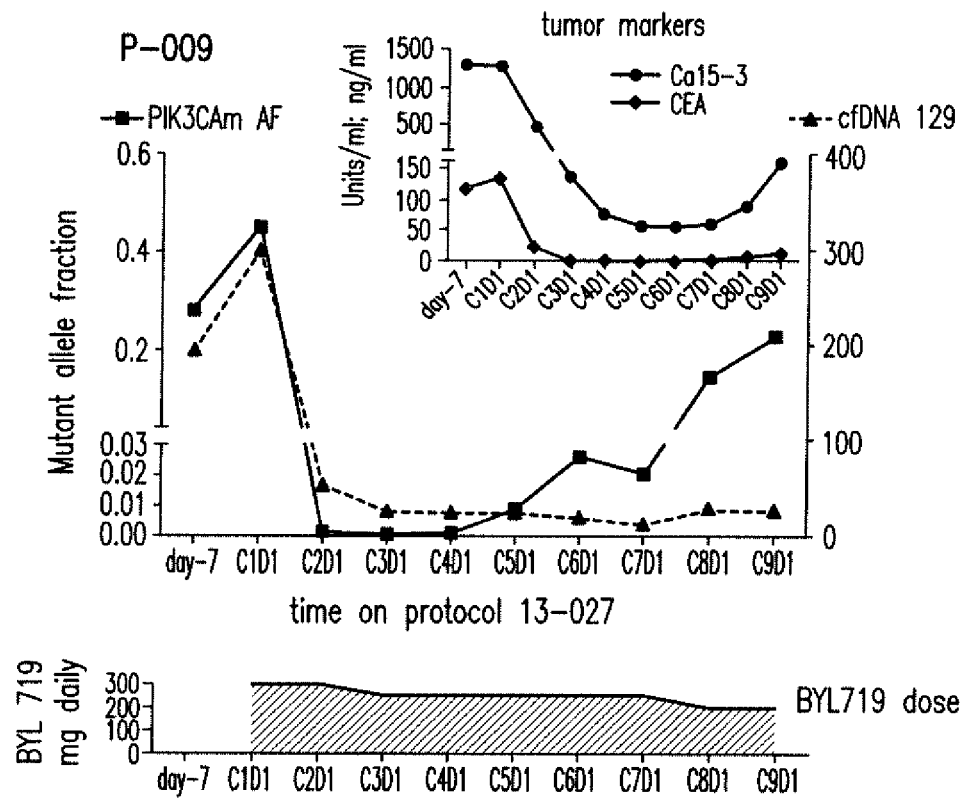
FIG. 5 shows that following treatment with BYL719 and letrozole, the cell free PIK3CA mutant allele fraction decreased markedly in patient 009.
Figure 5:
Figure 5:
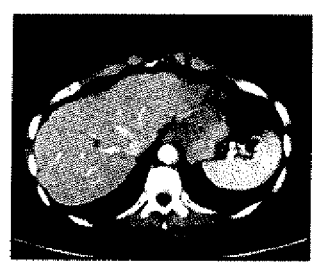

In patient 009, who has been treated with 8 chemotherapy and 4 anti-estrogen regimens, displayed a significant decrease in cfPIK3CA E542K mutant allele fraction in response to treatment with BYL719 and letrozole. At day 28, ddPCR quantifies a 99.7% decrease in the cfPIK3CA mutant allele fraction with no mutation detected at C3 and C4, despite a dose reduction (FIG. 5). The mutant allele fraction of PIK3CA E542K in patient 009 decreased from 0.4507 at day 1 to 0.0014 at day 28 (TABLE 2 and FIG. 5). Although an upward trend in mutant allele fraction has been identified since C5, the patient's response to treatment has continued. Next-generation sequencing has identified 2 activating PIK3CA mutations (E542K and E543K) in patient 009. CT scan of the patient prior to treatment displayed extensive hepatic tumor burden. At C3D1, C5D1 and C8D1, patient exhibited a partial response (PR) by RECIST criteria by CT scan (FIG. 5). By contrast, patient 008 which exhibited a 19.6% decrease in mutant allele fraction between day 1 and day 28 displayed a progression of the disease (TABLE 2). In patient 008, the marked 12.5 fold increase in H1047R mutant allele fraction at week 8 (C3D1) correlated with tumor progression, which was confirmed by CT imaging (FIGS. 2 and 4). These results are also displayed in FIG. 4 and indicate that the measurement of the cfPIK3CA mutant allele fraction at day 28 of treatment is predictive for clinical benefit with the PI3Kα inhibitor BYL719 and aromatase inhibition.

Figure 6:
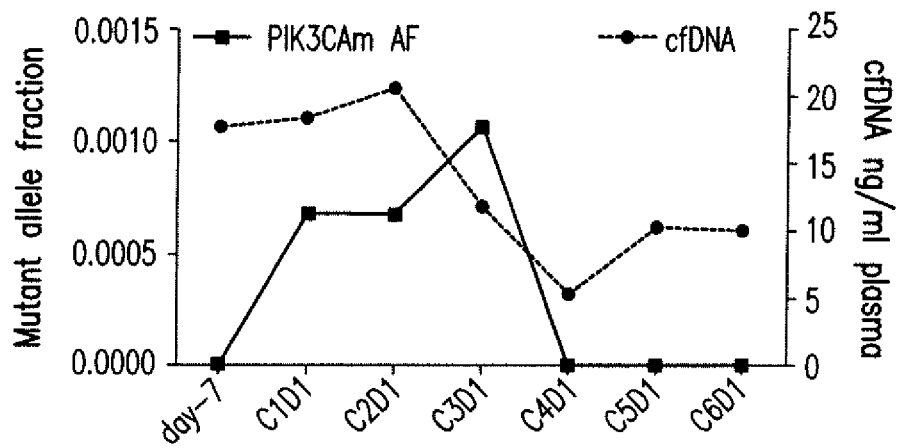
FIG. 6 shows that ddPCR is sensitive for detecting low levels of cell free PIK3CA mutant allele fractions.
Figure 7:
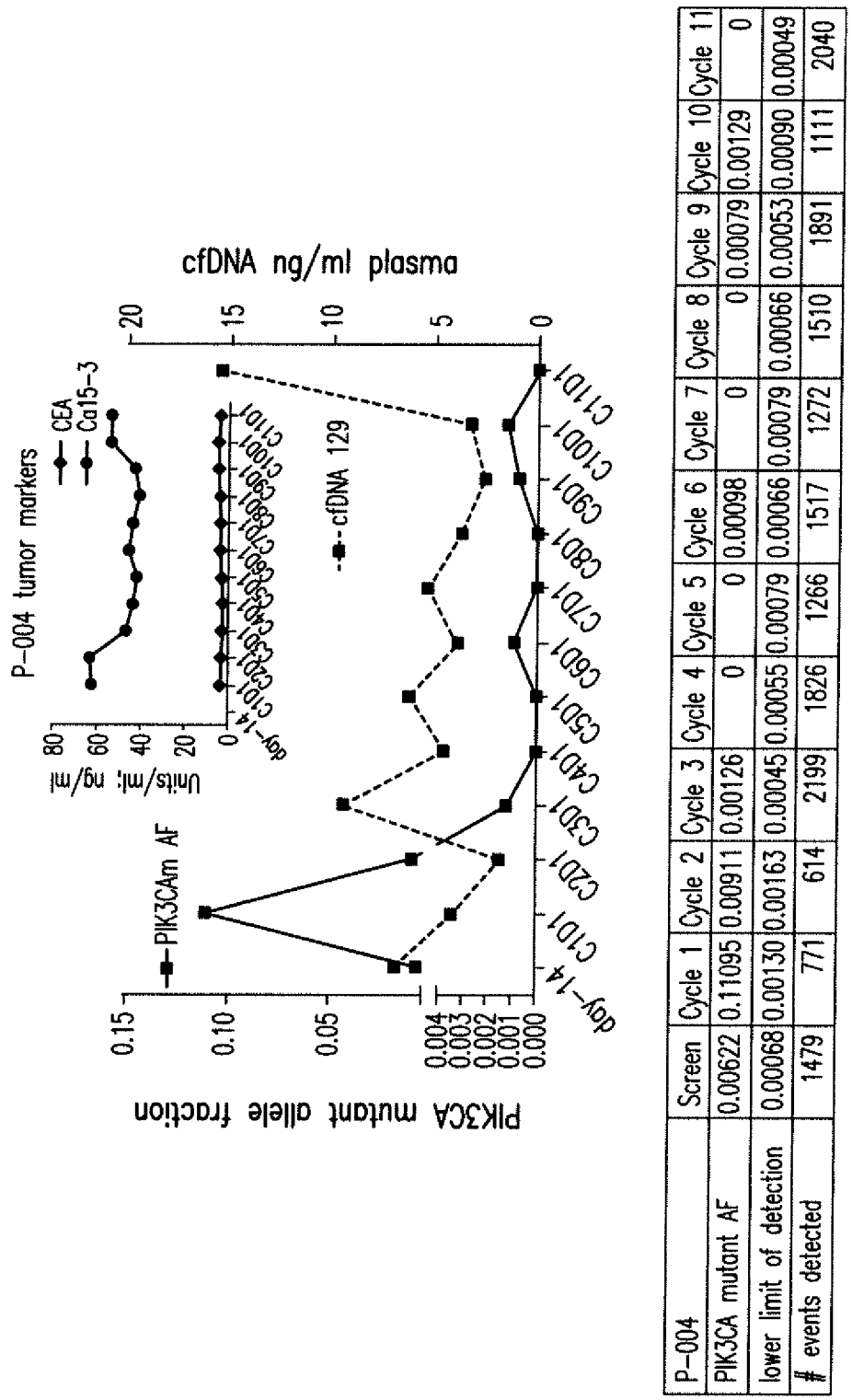
FIG. 7 shows that low total cfDNA concentrations were informative for determining and following cell free PIK3CA mutant allele fraction.

As shown in TABLE 2 and FIG. 6, ddPCR was sensitive for detecting low levels of PIK3CA mutant alleles. Mutant allele fractions as low as 0.00068 and 0.00107 were detected (FIG. 6). Despite low concentrations of total cfDNA, similar to levels identified in patients without cancer, serial cfPIK3CA mutant allele fraction measurements were informative. For example, in patient 004, the total cfDNA was measured to be ~6 ng/ml plasma before treatment, yet 11% of detected PIK3CA alleles are mutant (FIG. 7). A 91.8% decrease at C2D1 and 98.9% at C3 in cfPIK3CA mutant allele fraction was observed following treatment and these significant decreases in cfPIK3CA mutant allele fraction correlated with the patient's ongoing stable disease. After cycle II, the cfPIK3CA mutant allele fraction continued to be >99% decreased or undetectable (FIG. 7).

TABLE 1

| 13-027 Patient ID | Sites of metastatic disease | Tumor genotyping method | PIK3CA genotype | Mutant allele | cfDNA ng/ml plasma day 1 | ddPCR cfPIK3CA mutant detection |
|---|---|---|---|---|---|---|
| 001 | bone, liver, lung, adrenal | sequenom | wild-type | | | |
| 002 | bone, liver | sequenom | mutation | E545K | 328.9 | Yes |
| 003 | liver, LN | sequenom | wild-type | | | |
| 004 | bone | sequenom | mutation | E542K | 4.1 | Yes |
| 005 | bone | | not assessed | | 41.0 | |
| 006 | bone, liver | sequenom | wild-type | | 16.5 | |
| 007 | bone, liver, LN, breast | sequenom | mutation | H1047R | 20.4 | Yes |
| 008 | bone, liver, lung, brain, LN | NGS | mutation | H1047R | 112.3 | Yes |
| 009 | bone, liver, LN | sequenom | mutation | E542K | 595.4 | Yes |
| 012 | bone, liver, lung, LN | sequenom | mutation | E542K | 3908.5 | Yes |
| 013 | solitary bone | sequenom | mutation | E545K | 18.4 | Yes |
| 014 | bone | sequenom | wild-type | | 8.9 | |
| 016 | bone, liver, lung, LN, breast | NGS | wild-type | | 45.3 | |
| 017 | bone, liver, lung, LN | sequenom | mutation | H1047L | 61.7 | Yes |

*Patient 012 was no the study for 7 days and only the day 1 sample was assessed by ddPCR.

TABLE 2

| 13-027 Patient ID | Sites of metastatic disease | Mutant allele | cfDNA ng/ml plasma day 1 | cfPIK3CA mutant AF day 1 | cfPIK3CA mutant AF day 28 | cfPIK3CA mutant AF % decrease day 28 | Best Clinical Response | Days on study | Off Study |
|---|---|---|---|---|---|---|---|---|---|
| 009 | bone, liver, LN | E542K | 595.4 | 0.4507 | 0.0014 | 99.7 | PR | 230 | |
| 007 | bone, liver, LN, breast | H1047R | 20.1 | 0.0705 | 0.0013 | 98.2 | SD | 199 | POD |
| 002 | bone, liver | E545K | 328.9 | 0.3590 | 0.0092 | 97.4 | MR | 88 | POD |
| 004 | bone | E542K | 4.1 | 0.1110 | 0.0091 | 91.8 | SD | 289 | |
| 017 | bone, liver, lung, LN | H1047L | 61.7 | 0.5854 | 0.1290 | 77.9 | SD | 146 | POD |
| 008 | bone, liver, lung, brain, LN | H1047R | 112.3 | 0.1052 | 0.0850 | 19.6 | POD | 58 | POD |
| 013* | solitary bone | E545K | 16.4 | 0.0007 | 0.0007 | 0 | SD | 172 | |

*Changes in the mutant allele fraction at or near the lower limit of detection for the assay may not be reliable for interpretation.

Figure 8:
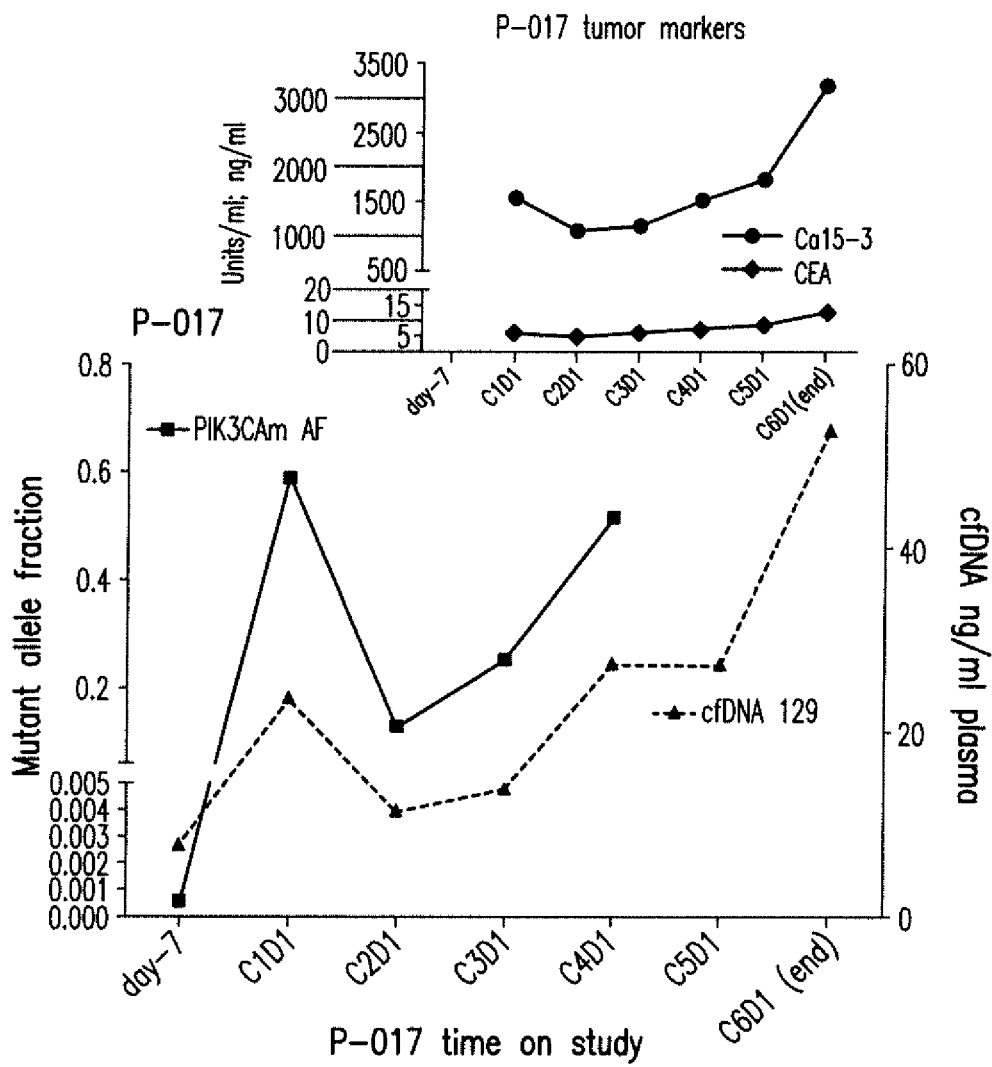
FIG. 8 shows that increases in the cell free PIK3CA mutant allele fraction may precede clinical progression by 1 to 3 months.
Figure 9:
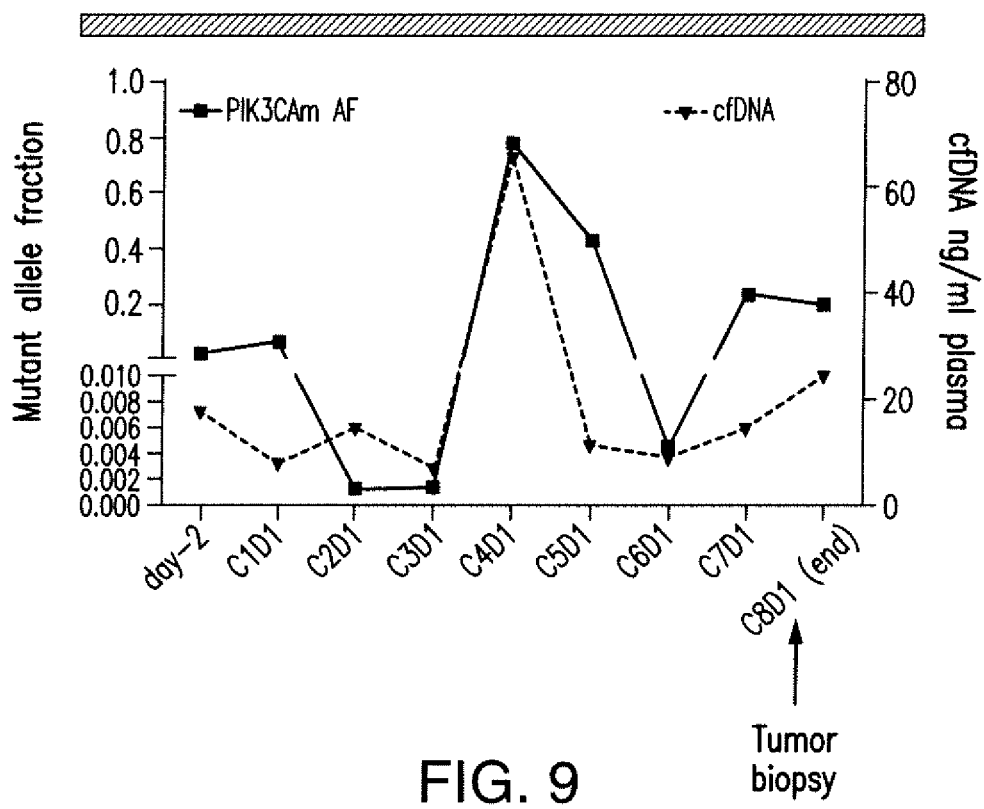
FIG. 9 shows that increases in the cell free PIK3CA mutant allele fraction may be used to determine early resistance to a PI3Kα inhibitor.

In patient 017, the cfPIK3CA mutant allele fraction decreased at day 28 (C2D1); however, the decrease was 78% as compared to other responders where the initial decrease was >90% (FIG. 8). This early decrease was followed by a progressive two-fold increase in the H1047L mutant allele fraction, although the patient had stable disease clinically and by imaging until progression of disease at cycle 6 (FIG. 8). These results suggest that increases in the cfPIK3CA mutant allele fraction may precede clinical progression by 1 to 3 months. Patient 017 harbored a tumor with a PIK3CA H1047L mutation, which is less activating than the H1047R hotspot mutation. The identification of such increases in mutant allele fraction may also be used to detect early resistance of the tumor to treatment by analysis of cfPIK3CA mutant alleles and can be used to determine the timing of tumor biopsies to perform further analysis of the tumor sample, e.g., by next-generation DNA sequencing (FIG. 9).

Further analysis of an additional 40 patients with tumors mutated for PIK3CA showed that in patients that exhibited a clinical benefit (e.g., exhibited six months of disease stability) to the PI3Kα inhibitor, an average decrease of 96.9% in the cfPIK3CA mutant allele fraction was observed during the first cycle of treatment. This average decrease in the cfPIK3CA mutant allele fraction was observed by day 7, day 14 or day 28 of treatment. In patients with a progression of disease, a transient decrease, no decrease or an increase was observed in the cfPIK3CA mutant allele fraction by ddPCR during the first cycle of treatment. In patients with a progression of disease, an average decrease of 25% in the cfPIK3CA mutant allele fraction was observed.

7.3. Discussion

Analysis of cfDNA in this Example, has demonstrated an early (day 28) and large (average 93%) decrease in cfPIK3CA mutant allele fraction at the first post treatment assessment in patients with stable and responsive disease. A patient with progressive disease exhibited a small (approximately 20%) and transient decrease in cfPIK3CA mutant allele fraction. A persistent disease in the cfPIK3CA mutant allele fraction associated with continued response. An increase in cfPIK3CA mutant allele fraction predicts for tumor resistance. Without being limited to a particular theory, the increase in cfPIK3CA mutant allele fraction may precede clinical progression by 1 to 3 months.

Incorporating cfPIK3CA mutant allele fraction assessment may be considered to identify early tumor response, identify evolving resistance prior to clinical progression, allow time tissue biopsy to assess samples arising resistance mechanisms. Dynamic changes in cfPIK3CA mutant allele fraction can be informative for developing personalized dosing strategies that limit toxicity and deter therapeutic resistance.

Various references are cited herein, the contents of which are hereby incorporated by reference in their entireties herein. Various nucleic acid and amino acid sequence accession numbers are cited herein, and the complete sequences referenced by those accession numbers are hereby incorporated by reference in their entireties herein.

What is claimed is:

1. A method for treating a subject having a breast cancer, comprising:
   (a) measuring a first PIK3CA mutant allele fraction in a sample from the subject obtained prior to a PI3Kα inhibitor treatment;
   (b) administering the PI3Kα inhibitor to the subject;
   (c) measuring a second PIK3CA mutant allele fraction in a sample from the subject obtained during the PI3Kα inhibitor treatment;
   (d) comparing the first PIK3CA mutant allele fraction with the second PIK3CA mutant allele fraction; and
   (e) continuing administering the PI3Kα inhibitor to the subject when an early tumor response is identified by the second PIK3CA mutant allele fraction being decreased greater than about 70% as compared to the first PIK3CA mutant allele fraction, or
   discontinuing the PI3Kα inhibitor when an evolving resistance prior to clinical progression is identified by the second PIK3CA mutant allele fraction being decreased less than about 25% as compared to the first PIK3CA mutant allele fraction,
   wherein the first and the second PIK3CA mutant allele fractions are the ratio of the copies of a PIK3CA mutant allele to the copies of a PIK3CA wild-type allele, and
   wherein the PI3Kα inhibitor is selected from the group consisting of BYL719, INK-1114, INK-1117, NVP-BYL719, SRX2523, LY294.002, PIK-75, PKI-587, A66, CH5132799 and GDC-0032, and
   wherein the first and the second PIK3CA mutant allele fractions comprise a PIK3CA mutation selected from the group consisting of H1047R, E545K, E542K, E545G, E545Q, E545A, E545D, E545V, H1047L, H1047Y, E542Q, E542G, P539R, N345K, C420R, G1049R, E726K, R88Q, Q546K, Q546P, Q546R, Q546L, and combinations thereof.

2. The method of claim 1, wherein the decrease in the second PIK3CA mutant allele fraction is greater than 90% as compared to the first PIK3CA mutant allele fraction.

3. The method of claim 1, wherein the first and the second PIK3CA mutant allele fractions are determined by polymerase chain reaction.

4. The method of claim 1, wherein the samples are plasma samples.

5. The method of claim 1, wherein multiple samples are serially obtained from the subject during the PI3Kα inhibitor treatment, at about every four weeks after initiation of the PI3Kα inhibitor treatment.

6. The method of claim 1, wherein multiple samples are serially obtained from the subject during the PI3Kα inhibitor treatment, at about every two weeks after initiation of the PI3Kα inhibitor treatment.

7. The method of claim 1, wherein multiple samples are serially obtained from the subject during the PI3Kα inhibitor treatment, at about every week after initiation of the PI3Kα inhibitor treatment.

8. The method of claim 1, wherein the first and the second PIK3CA mutant allele fractions comprise a PIK3CA mutation selected from the group consisting of: mutations in a PIK3A kinase domain, mutations in a PIK3CA C2 domain, mutations in a PIK3CA helical domain, and combinations thereof, wherein the PIK3CA mutation increases PIK3CA activity.

9. The method of claim 1, wherein the first and the second PIK3CA mutant allele fractions comprise the PIK3CA mutation E542K.

10. The method of claim 1, wherein the breast cancer is metastatic breast cancer.

11. The method of claim 1, wherein the PI3Kα inhibitor is BYL-719.

12. The method of claim 1, wherein the sample is a cell-free genomic DNA sample.

* * * * *